United States Patent [19]

Hayes et al.

[11] Patent Number: 5,518,757

[45] Date of Patent: May 21, 1996

[54] 4-ALLYLANISOLE ANALOG SCOLYTID REPELLENTS

[75] Inventors: Jane L. Hayes; Brian L. Strom, both of Pineville; Lawrence Roton, Pollock, all of La.; Leonard L. Ingram, Jr., Starkville, Miss.

[73] Assignees: The United States of America as represented by the Department of Agriculture, Washington, D.C.; Mississippi State University, Miss.

[21] Appl. No.: 358,707

[22] Filed: Dec. 19, 1994

Related U.S. Application Data

[63] Continuation-in-part of Ser. No. 113,709, Aug. 31, 1993, Pat. No. 5,403,863.

[51] Int. Cl.$^6$ .......................... A01N 25/00; A01N 25/08; A01N 31/14; A01N 25/18

[52] U.S. Cl. .............................. 427/4; 424/405; 424/409; 514/919

[58] Field of Search .................................. 427/4; 424/84, 424/405, 409; 514/919

[56] References Cited

U.S. PATENT DOCUMENTS

| | | | |
|---|---|---|---|
| 3,876,762 | 4/1975 | Rabussier et al. | 424/78 |
| 4,017,030 | 4/1977 | Coplan et al. | 239/44 |
| 4,170,631 | 10/1979 | Young et al. | 424/19 |
| 4,176,189 | 11/1979 | Itaya et al. | 424/273 R |
| 4,219,570 | 8/1980 | Inazuka et al. | 424/343 |
| 4,732,899 | 3/1988 | Gehret et al. | 514/245 |
| 4,774,081 | 9/1988 | Flashinski et al. | 424/78 |
| 4,839,383 | 6/1989 | Vité | 514/456 |
| 5,116,862 | 5/1992 | Weston | 514/346 |
| 5,281,418 | 1/1994 | Lindgren et al. | 424/405 |
| 5,314,693 | 5/1994 | Suga | 424/196.1 |
| 5,418,164 | 5/1995 | Andersch et al. | 435/254.1 |

OTHER PUBLICATIONS

G. Gries et al., Journal of Economic Entomology, New Techniquest for Capturing and Analyzing Se–miochemicals for Scolytid Beetles, vol. 81, No. 6, pp. 1715–1720. 1988, (no month available).

J. L. Hayes et al., Identification of a Host Compound and It's Practical Applications: 4–allyla nisole as a Bark Beetle Repellent, Paper presented Feb. 1–2, 1994, 12 pages.

ACS Abstract 116:53706 of DE 4012224 A1, "Honeybee Repellants . . . ", Heinrich Holtman, Oct. 1991.

J. Agric. Food Chemistry, Liu et al., "Volatiles from the Foliage of Soybean, Glycine Max and Lima Bean, Phaseolus lunatus: Their Behavioral Effects on the Insects *Trichoplusia ni* and *Epilachna varivestis*", vol. 37(2), pp. 496–501, 1989 (no month).

Primary Examiner—Diana Dudash
Attorney, Agent, or Firm—Oblon, Spivak, McClelland, Maier & Neustadt

[57] ABSTRACT

4-allylanisole, and three analogs, anisole, allylbenzene, and 4-isopropylanisole are demonstrated to be effective repellents for scolytid infestation. Conifers, a particular target for the scolytids, are protected by application of the compounds, either directly or suspended in a carrier.

4 Claims, 2 Drawing Sheets

4-ALLYLANISOLE ANALOG SCOLYTID REPELLENTS

RELATED PATENT APPLICATIONS

This application is a continuation-in-part application of U.S. patent application Ser. No. 08/113,709 filed Aug. 31, 1993, now U.S. Pat. No. 5,403,863. The entire disclosure of that application is incorporated herein, by reference.

BACKGROUND OF THE INVENTION

In applicants' pending application U.S. Ser. No. 08/113, 709 filed Aug. 31, 1993, the effectiveness of 4-allylanisole as a repellent for Scolytidae in general is examined at length. Insect attack on healthy, damaged or weakened host trees, such as loblolly pines and other host trees (including e.g. all yellow pines including eastern and western species, eastern and western white pines, Norway spruce, Larch, eastern red cedar, eastern Hemlock, Fraser fir, Douglas fir, and other fir trees, and thus generally conifers) continues to be a significant commercial and ecological problem. Although certain insecticides have been established for limited protection of trees, the use of non-natural chemical insecticides itself has serious impacts on the environment, and ought be avoided, where possible. In particular, the use of a limited number of chemicals increases the risk of development of resistance in the pest population, alters the ecosystem by reducing species diversity, modifying the food chain and altering patterns of energy flow and nutrient cycling, and may adversely affect natural enemies of the pests, (the southern pine beetle, and members of the beetle family, Scolytidae in general). Coupled with the ecological dangers of using an insecticide is the fact that the high cost of labor and the high cost of the chemical products, along with the need to spray all surfaces for effective control, will generally restrict the use of topically applied chemicals. Thus, applicants' identification in the parent application of 4-allylanisole as a repellent to scolytids, a naturally produced component of the resin exuded by the potential host, provides an alternate method of protecting these hosts, which does not require spraying of all potential surfaces. In particular, application of the product as a concentrated liquid, carried on elution devices or applied directly to a portion of the tree, or as a vapor, may be used with good effectiveness.

The prior art in this field is, as a result of the desirability of selecting naturally-produced products, focused on components of resins produced by the host trees. Of all the references discussed in the parent application, *Werner, Journal of Insect Physiology*, 18:423–438, 1972 is perhaps the most complete. This reference identifies 4-allylanisole as an attractant for *Ips grandicollis* in purified form at 1% concentration. The article teaches one of skill in the art that an effective repellent for Scolytidae employing 4-allylanisole cannot be prepared. However, additional research by the author of the reference, Werner, *Environmental Entomology*, (in press) has in fact documented the discovery disclosed in the pending parent application, that 4-allylanisole is a repellent for scolytids.

Accordingly, it remains an object of those of skill in the art to develop alternatives to conventional insecticides, employing compounds selected from, or similar to, those naturally produced by the targeted host, as effective insect repellents.

SUMMARY OF THE INVENTION

Applicants' invention resides in the discovery that analogs of 4-allylanisole are as effective as 4-allylanisole in repelling southern pine beetle as well as related scolytids. Specifically, anisole, allylbenzene, and 4-isopropylanisole each repel in excess of 90% of the southern pine beetles exposed to the same, in laboratory tests established as having a high correspondence with field trials. Surprisingly, other closely related analogs showed little or no repellency when tested under identical conditions. 4-allylanisole, as well as the 3 analogs named above can be prepared in the form of an insect repellent for the protection of conifers subject to scolytid attack. Methods of controlling scolytid attack using these effective compounds, which are either naturally produced or closely correlated thereto, include applying the chemical to the surface of the tree or other host, or applying solid supports, such as cloth wicks from which the repellent chemical is eluted, or dispersed as vapor, in areas proximate to the surface from which the scolytids are to be repelled. Specific trees, bearing vulnerable wounds, such as those produced by lightning strikes and woodpecker activity, can be protected by application to the exposed area. Similarly, single trees, and stands of trees can be protected by the effective use of these environmentally-neutral compounds.

DETAILED DESCRIPTION OF THE INVENTION

To test the effectiveness of insect repellents, a laboratory assay is employed, which assay has been demonstrated to be highly correlated with field trials Hayes et al., *J. Chem. Ecol.* 20(7): 1595–1615, 1994 and Hayes & Strom, *J. Economic Entomology* 87(6) 1586–1594, 1994. Specifically, a circle (17 cm in diameter by 5 mm wide) of the potential repellent is painted with a camel-hair brush on a 28×21.5-cm piece of uncoated cardboard. Aftesr 3 minutes, beetles (2–5 individuals) are released in the center of the treated circle. Testing was conducted at room temperature with light supplied from an adjoining room. To prevent overwhelming photopositive responses, an object was used to cast a shadow over the test circle. Beetles were briefly refrigerated prior to testing to reduce their tendency to fly. Responses (up to a 30 second exposure) were recorded as not-repelled or repelled: not-repelled beetles walk through the circle are stopped but proceeded across the circle within 30 seconds of exposure; and repelled beetles stopped abruptly, raised antennae (some "reared up" on hind legs), stood motionless and/or moved away from the circle (some moved abruptly in the opposite direction).

Trials were conducted with newly emerged male and female southern pine beetles on three different dates from three different source populations. The results of these trials (n=300) were combined for presentation in FIG. 1. Trials were also conducted with the clerid beetle *T. dubius*, a common predator of the southern pine beetle and other scolytid species. In all trials, only apparently healthy beetles were used.

Figure 1:
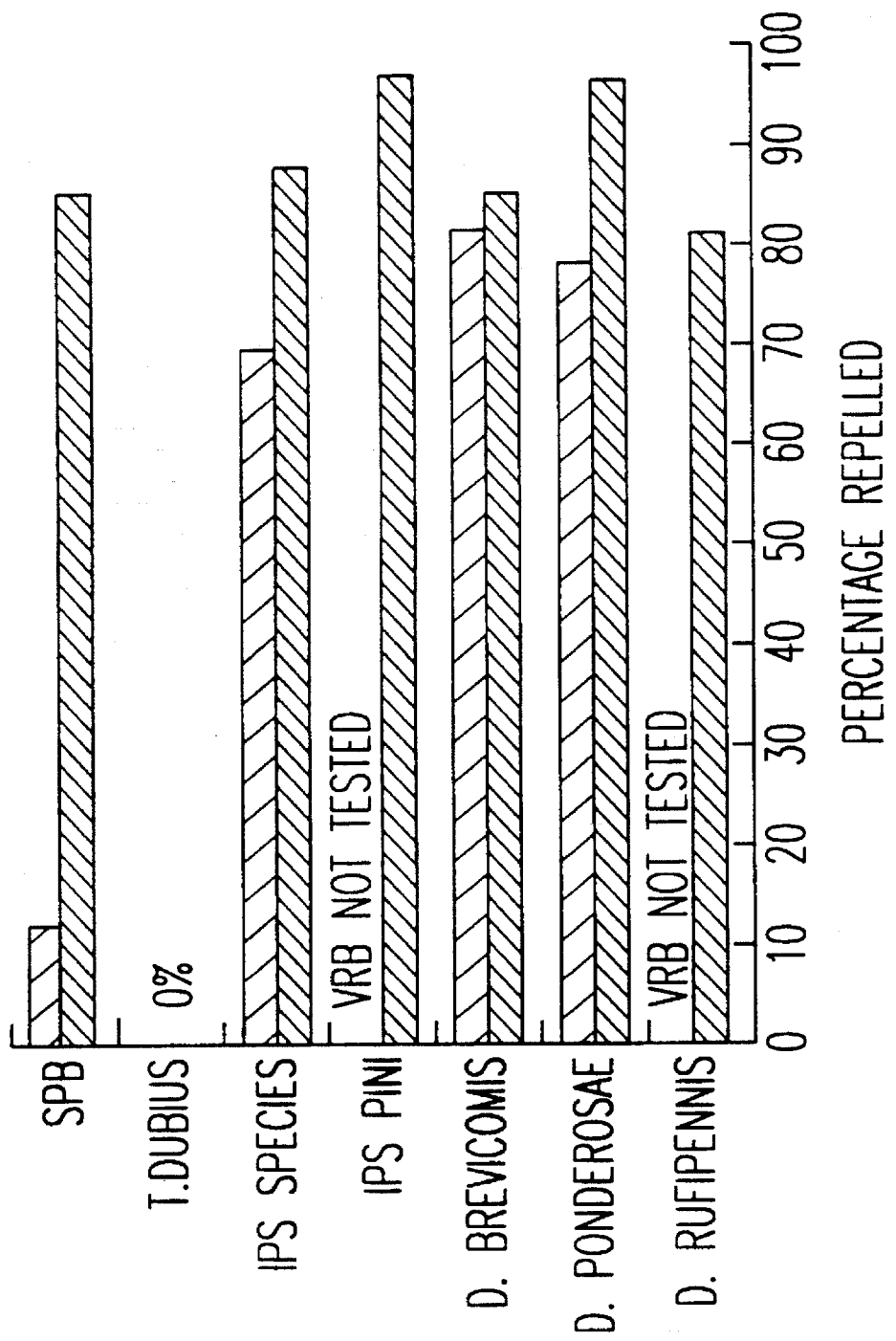
FIG. 1 is a graphic summary of the response, percent repelled, of southern pine beetles and other scolytid species to 4-allylanisole. This response is shown in black bars, and compared with the response (% repelled) to the most widely used semiochemical, an anti-aggregation pheromone, verbenone, shown in shaded bars in laboratory assays. The repellents were also tested against *Thanasimus dubius*, a clerid, which is a predator of scolytid species.

As is clearly shown in FIG. 1, well over 80% of all species of scolytid were at least as effectively repelled by 4-allylanisole as commercially and experimentally available compounds, amounts much greater than those repelled by the experimentally available anti-aggregant, verbenone. In point of fact, against the southern pine beetle (SPB), verbenone was remarkably ineffective, repelling less than 15% of the time, while 4-allylanisole gave an approximate 90% repellency value.

To identify analogous repellents, chemical analogs of 4allylanisole were obtained and tested according to the laboratory assay described above. The analogs include anisole, allylbenzene, trans-anethole, 4-isopropylanisole, 4-methoxycinnamonitrile, 4-methoxyphenylacetonitrile and eugenol. As can be seen from FIGS. 2 and 3, these analogs bear a close resemblance to 4-allylanisole, in combining one or both of the substituent groups of 4-allylanisole on a single phenyl ring, as well as introducing other familiar substituents, such as the isopropyl moiety and the widely effective nitrile substituent.

Figure 2:
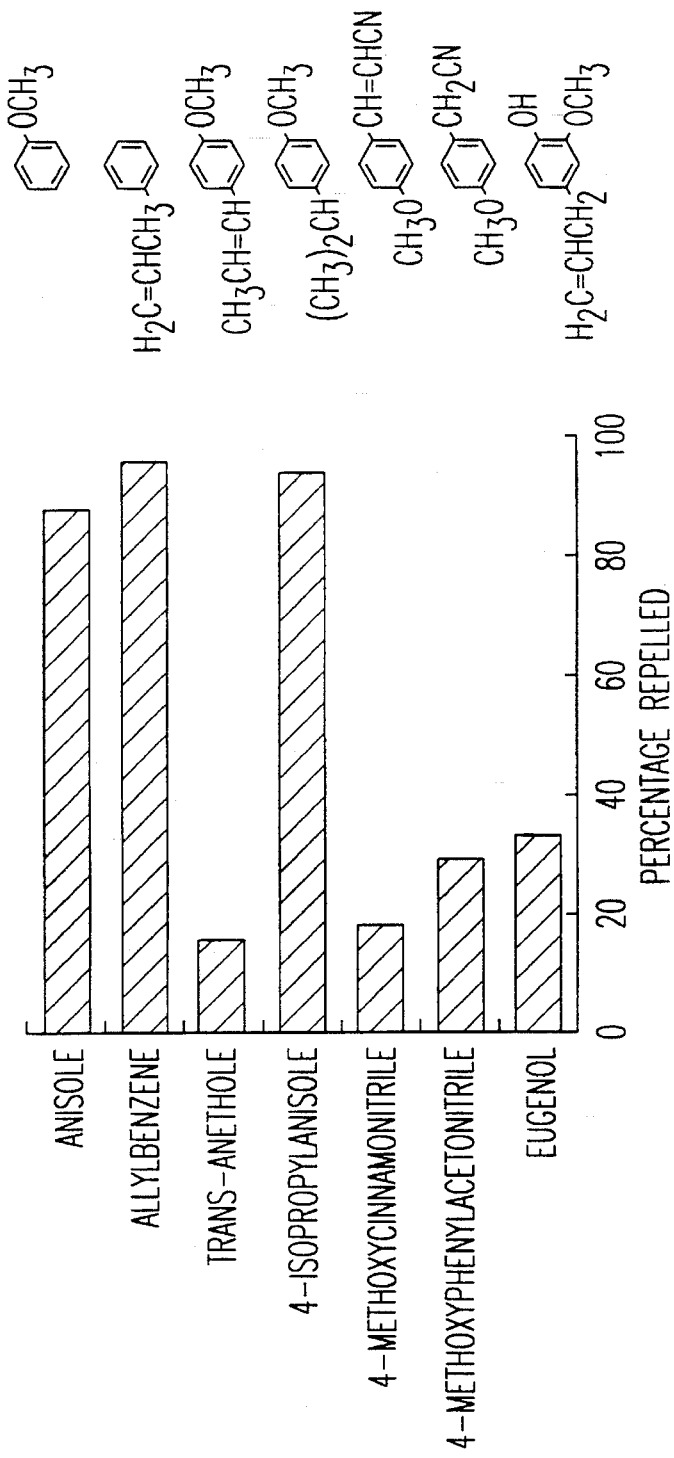
FIG. 2 is a graphic depiction of the response of southern pine beetles to chemical analogs of 4-allylanisole, giving the analog structures. The percentage of beetles repelled is shown in black bars.
Figure 3:
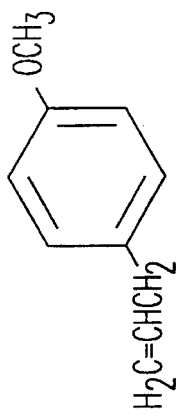
FIG. 3 gives the structure of 4-allylanisole.

The result of the testing is set forth in FIG. 2. Surprisingly, three of the analogs performed as well or better than 4-allylanisole in repelling over 90% of the insects. Anisole, allylbenzene and 4-isopropylanisole proved remarkably effective as repellents for the southern pine beetle. Equally surprising, four other closely related analogs were not demonstrated to be effective in repelling the scolytids. The essential characteristic of the chemical structure of a scolytid repellent is not apparent from these tests alone. While it appears that either the methoxy or allyl group of 4-allylanisole is a requirement for repellency, the presence of both surprisingly leads to an ineffective compound, eugenol.

The laboratory studies conducted have been well documented as effective predictors of field performance. These studies include protection of at risk pine trees with the inventive repellents such as lightning-struck pine trees or pine trees with cavities due to red-cockaded wood pecker activity. No protected trees were attacked by any scolytid. Additionally, 90% protection of threatened pines at the urban/forest interface was achieved. This, as well as the results of independent investigators, Werner, Env. Ent. (in press), have led those in the field to conclude that the laboratory assay described above is recognized as a valid determinant of a species response.

Of further importance is the fact the repellents of this invention, 4-allylanisole and the effective analogs, do not repel, and apparently do not affect, a predator of scolytids, the clerid beetle *T. dubius*. Thus, the repellents of the claimed invention, either a chemical naturally produced by target conifer hosts, or chemical analogs thereof, are environmentally sound, at least as effective as the predominant experimental compound available, insect-produced anti-aggregant verbenone and provide a compelling alternative to insecticides in that they do not disturb naturally-occurring predators. Thus, these compounds are superior biologically-efficient conifer-protectants.

The repellent can be prepared either as a neat preparation, admixed with an environmentally compatible carrier, or as a solid wick or polymer mass impregnated with the repellent compound which is released therefrom. Application of sprays and prepared suspensions to trees may additionally be effective. Concentrations can range from 0.01% up to 100%.

This invention has been disclosed and described above with reference to both specific examples and generic concept. Alternatives will occur to those with skill in the art, particularly with respect to concentration, environmentally compatible carrier and method of administration, without departing from the scope of the invention, save as limited by the claims set forth below.

What is claimed is:

1. A method of repelling scolytids from a surface subject to attack by said scolytids, comprising applying a repellent compound selected from the group consisting of anisole, allylbenzene, 4-isopropylanisole and mixtures thereof in amounts sufficient to repel said scolytids from said surface or eluting said compound in amounts sufficient to repel said scolytids from said surface from solid supports adjacent to said surface from which said scolytids are to be repelled.

2. A method of protecting tree hosts from attack by scolytids comprising applying a repellent compound selected from the group consisting of anisole, allylbenzene, 4-isopropylanisole and mixtures thereof to trees subject to attack by scolytids in concentrations sufficient to repel said scolytids.

3. The method of claim 2, wherein said scolytids comprise those insects in the family Scolytidae that attack coniferous hosts.

4. The method of claim 2 wherein said tree host comprises conifers.

* * * * *